United States Patent
Coon et al.

(10) Patent No.: US 10,055,817 B2
(45) Date of Patent: Aug. 21, 2018

(54) SYSTEMS AND METHODS FOR DETERMINING PUPILLARY DISTANCE AND SCALE

(71) Applicant: glasses.com Inc., Mason, OH (US)

(72) Inventors: Jonathan Coon, Austin, TX (US); Darren Turetzky, Cedar Park, TX (US); Ryan Engle, Pflugerville, TX (US)

(73) Assignee: glasses.com Inc., Mason, OH (US)

( * ) Notice: Subject to any disclaimer, the term of this patent is extended or adjusted under 35 U.S.C. 154(b) by 85 days.

(21) Appl. No.: 14/708,032

(22) Filed: May 8, 2015

(65) Prior Publication Data
US 2015/0323310 A1 Nov. 12, 2015

Related U.S. Application Data (60) Provisional application No. 61/990,556, filed on May 8, 2014.

(51) Int. Cl.
| | |
|---|---|
| *G06K 9/52* | (2006.01) |
| *G06T 3/40* | (2006.01) |
| *G06K 9/00* | (2006.01) |
| *G06K 9/20* | (2006.01) |

(52) U.S. Cl.
CPC .......... *G06T 3/4092* (2013.01); *G06K 9/0061* (2013.01); *G06K 9/209* (2013.01); *G06K 9/52* (2013.01); *G06T 3/40* (2013.01)

(58) Field of Classification Search
CPC ........ G01B 11/14; G01B 11/00; G01B 21/02; G06K 9/6202; G06T 3/40
See application file for complete search history.

(56) References Cited

U.S. PATENT DOCUMENTS

| | | | |
|---|---|---|---|
| 6,535,223 B1 | 3/2003 | Foley | |
| 8,064,647 B2 | 11/2011 | Bazakos et al. | |
| 2008/0292151 A1* | 11/2008 | Kurtz | A61B 3/10 382/128 |

(Continued)

FOREIGN PATENT DOCUMENTS

| | | | |
|---|---|---|---|
| FR | 2966038 A1 | 4/2012 | |
| WO | WO 2001/023908 A1 | 5/2001 | |

(Continued)

OTHER PUBLICATIONS

International Search Report and Written Opinion of the International Searching Authority directed to related International Patent Application No. PCT/US2015/030011, dated Jul. 31, 2015; 11 pages.

(Continued)

*Primary Examiner* — Obafemi Sosanya
(74) *Attorney, Agent, or Firm* — Sterne, Kessler, Goldsein & Fox, P.L.L.C.

(57) ABSTRACT

A computer-implemented method for scaling an object is described. A distance of an object from the computing device is measured via a processor of a computing device in conjunction with a rangefinder. An image of the object is captured via the processor. A database of pixel densities is queried, via the processor, for a pixel density at the measured distance of the object from the computing device. A depiction of the object is scaled based on determining a distance of a detected feature of the object.

18 Claims, 9 Drawing Sheets

(56) References Cited

U.S. PATENT DOCUMENTS

| | | |
|---|---|---|
| 2009/0097716 A1 | 4/2009 | Wang et al. |
| 2011/0267578 A1 | 11/2011 | Wilson |
| 2013/0141468 A1 | 6/2013 | Coon |
| 2013/0194289 A1* | 8/2013 | Snow ....................... G09G 5/14 345/581 |
| 2013/0278895 A1 | 10/2013 | Pham et al. |
| 2013/0314413 A1 | 11/2013 | Coon et al. |

FOREIGN PATENT DOCUMENTS

| | | |
|---|---|---|
| WO | WO 2009/007731 A1 | 1/2009 |
| WO | WO 2015/172097 | 11/2015 |

OTHER PUBLICATIONS

Extended European Search Report for EP Application No. 15789361.1, dated Dec. 11, 2017; 1 page.

* cited by examiner

SYSTEMS AND METHODS FOR DETERMINING PUPILLARY DISTANCE AND SCALE

RELATED APPLICATIONS

This application claims priority to U.S. Application No. 61/990,556, entitled SYSTEMS AND METHODS FOR DETERMINING PUPILLARY DISTANCE AND SCALE, filed on May 8, 2014, which is incorporated herein in its entirety by this reference.

BACKGROUND

The use of computer systems and computer-related technologies continues to increase at a rapid pace. This increased use of computer systems has influenced the advances made to computer-related technologies. Indeed, computer systems have increasingly become an integral part of the business world and the activities of individual consumers. Computers have opened up an entire industry of internet shopping. In many ways, online shopping has changed the way consumers purchase products. For example, a consumer may want to know what they will look like in and/or with a product. On the webpage of a certain product, a photograph of a model with the particular product may be shown. However, users may want to see more accurate depictions of themselves in relation to various products.

SUMMARY

According to at least one embodiment, a computer-implemented method for scaling an object is described. A distance of an object from the computing device may be measured via a processor of a computing device in conjunction with a rangefinder. An image of the object may be captured via the processor. A database of pixel densities may be queried, via the processor, for a pixel density at the measured distance of the object from the computing device.

In one embodiment, a feature of the object may be detected. A number of pixels associated with the detected feature of the object may be determined. A distance associated with the detected feature of the object may be determined based on a quotient resulting from dividing the number of pixels associated with the detected feature of the object by the queried pixel density at the measured distance of the object. A depiction of the object may be scaled based on the determined distance associated with the detected feature of the object. In some embodiments, detecting a feature of the object may include detecting a pupil of a user. In one embodiment, determining a distance associated with the detected feature may include determining a pupil distance of the user.

In some embodiments, a sensor pixel density of the sensor may be determined. A pixel density of an image captured by the camera of the computing device may be determined for a predetermined distance from the computing device based at least on the sensor pixel density of the sensor. The determined pixel density for each predetermined distance from the computing device may be stored in the database.

A computing device configured to scale an object is also described. The device may include a processor and memory in electronic communication with the processor. The memory may store instructions that are executable by the processor to measure, in conjunction with a rangefinder of the computing device, a distance of an object from the computing device, capture an image of the object, and query a database of pixel densities for a pixel density at the measured distance of the object from the computing device.

A computer-program product to scale an object is also described. The computer-program product may include a non-transitory computer-readable medium that stores instructions. The instructions may be executable by a processor to measure, in conjunction with a rangefinder of the computing device, a distance of an object from the computing device, capture an image of the object, and query a database of pixel densities for a pixel density at the measured distance of the object from the computing device.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

In various situations, it may be desirable to scale an object. For example, it may be desirable to scale a two-dimensional (2D) model and/or image of a user. Likewise, it may be desirable to scale a three-dimensional (3D) model of a user so that two or more 3D models may be mated and scaled according to a common scale. For instance, the systems and methods described herein may allow for proper scaling of 3D models when virtually tying-on products (e.g., virtually trying-on a pair of glasses). Accordingly, a scaled 3D model of the user may be mated with a scaled 3D model of a pair of glasses. Although examples used herein may describe the scaling of a user and/or a pair of glasses, it is understood that the systems and methods described herein may be used to scale a model of any object.

Figure 1:
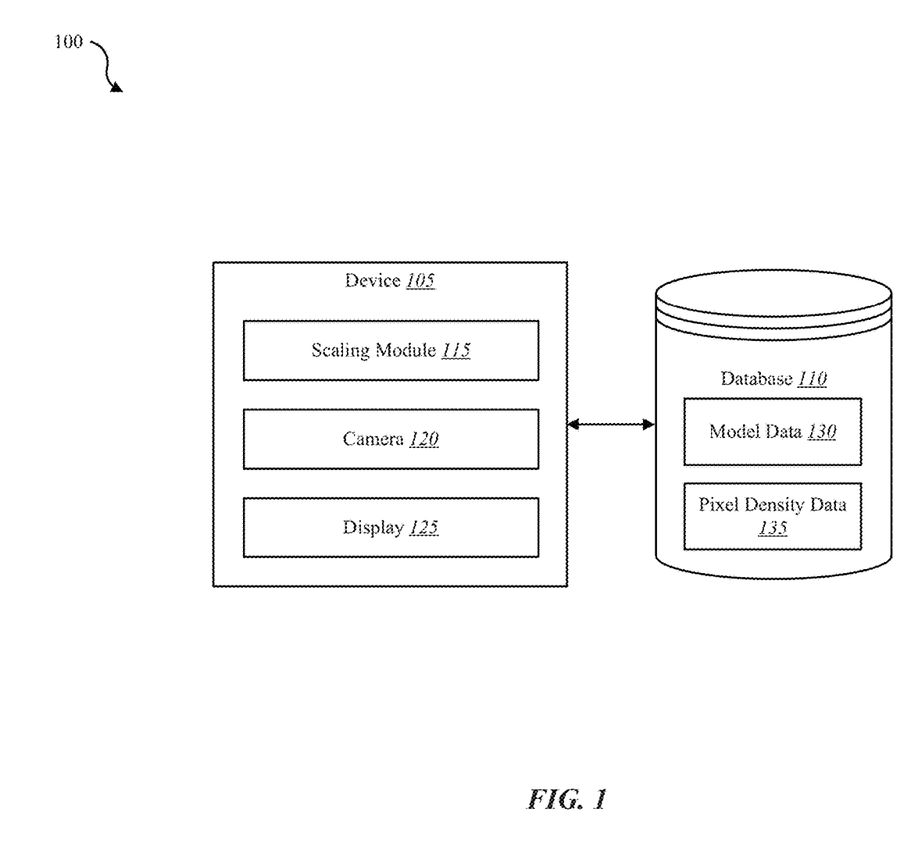
FIG. 1 is a block diagram illustrating one embodiment of an environment in which the present systems and methods may be implemented.

FIG. 1 is a block diagram illustrating one embodiment of an environment 100 in which the present systems and methods may be implemented. In some embodiments, the systems and methods described herein may be performed on a single device (e.g., device 105). For example, the systems and method described herein may be performed by a scaling module 115 that is located on the device 105. Examples of device 105 include mobile devices, smart phones, personal computing devices, computers, servers, etc.

In some configurations, a device 105 may include the scaling module 115, a camera 120, and a display 125. In one example, the device 105 may be communicatively coupled to a database 110. In one embodiment, the database 110 may be internal to device 105. In one embodiment, the database 110 may be external to device 105. In some embodiments, portions of database 110 may be both internal and external to device 105. In some configurations, the database 110 may include model data 130 and pixel density data 135.

In one embodiment, the scaling module 115 may scale a model of an object. Scaling module 115 may scale a 3D model of an object, a 2D model of an object, an image of an object (e.g., a captured image, a 2D rendering of a 3D model, etc.), and so forth. In one example, scaling a 3D model of a user enables the user to view an image on the display 125 of the scaled, 3D model of the user in relation to another 3D object. For instance, the image may depict a user virtually trying-on a pair of glasses with both the user and the glasses being scaled according to a common scaling standard determined by scaling module 115. Thus, scaling module 115 may scale the 3D model of the user and the 3D model of the pair of glasses, such that the glasses appear in proper scale in relation to the user as they would if the user were to wear an actual pair of the glasses. The scaled models may then be mated to render a 2D image of the user wearing the glasses.

Scaling module 115 may store scaling information in database 110. Thus, model data 130 may include scaling information determined by scaling module 115, image data captured by camera 120, information and data regarding a model of a user, information and data regarding a model of an object, and algorithms used by scaling module 115 to determine one or more distances in a particular unit of distance associated with an image of a user captured by camera 120. Pixel density data 135 may include information and data regarding a camera sensor, including the sensor size, a pixel density or resolution of the sensor (e.g., 1,280 horizontal pixel count by 960 vertical pixel count for a 1.2 megapixel (MP) sensor, etc.), a pixel density of an image (e.g., horizontal and vertical pixels in the image), a pixel density per unit length from the camera (e.g., the number of pixels per inch for an object that is a certain number of inches from the camera when an image of the object is captured, such as 100 pixels per inch when the depth of the object from the camera is 12 inches at the time the image is captured, etc.), and so forth.

Accordingly, in one embodiment, the 3D model of an object and/or user may be obtained based on the model data 130. In one example, the model data 130 may be based on an average model that may be adjusted according to measurement information determined about the object (e.g., a morphable model approach). In one example, the 3D model of the object and/or user may be a linear combination of the average model. In some embodiments, the model data 130 may include one or more definitions of color (e.g., pixel information) for the 3D model. In one example, the 3D model may have an arbitrary size. In some embodiments, the scaled 3D model (as scaled by the systems and methods described herein, for example) may be stored in the model data 130. In some cases, a rendered, 2D image based on the scaled 3D model may be displayed via the display 125. For example, an image of a virtual try-on based on the scaled 3D representation of a user and a 3D model of glasses scaled according to determined scaling may be displayed on display 125.

Figure 2:
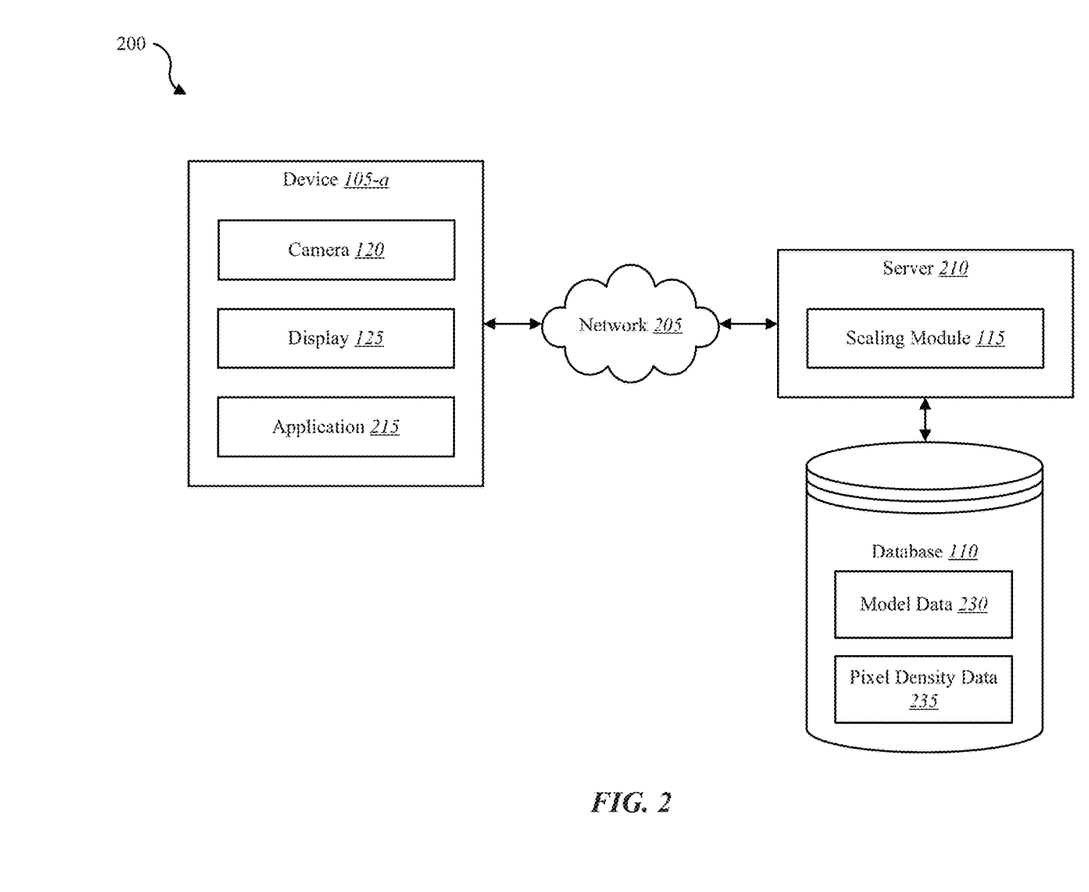
FIG. 2 is a block diagram illustrating another embodiment of an environment in which the present systems and methods may be implemented.

FIG. 2 is a block diagram illustrating another embodiment of an environment 200 in which the present systems and methods may be implemented. In some embodiments, a device 105-a may communicate with a server 210 via a network 205. Examples of networks 205 include local area networks (LAN), wide area networks (WAN), virtual private networks (VPN), cellular networks (using 3G and/or LTE, for example), etc. In some configurations, the network 205 may be the internet. In some configurations, the device 105-a may be one example of the device 105 illustrated in FIG. 1. For example, the device 105-a may include the camera 120, the display 125, and an application 215.

In some embodiments, the server 210 may include the scaling module 115. In one embodiment, the server 210 may be coupled to the database 110. For example, the scaling module 115 (from device 105-a and/or server 210) may access the model data 130 in the database 110 via the server 210. The database 110 may be internal or external to the server 210, or both (e.g., a copy of model data 130 and/or pixel density data 135 stored on a storage device located in server and synchronized with the content on an external database 110). In some embodiments, the device 105-a may not include a scaling module 115. For example, the device 105-a may include an application 215 that allows device 105-a to interface with the scaling module 115 located on server 210. In some embodiments, both the device 105-a and the server 210 may include a scaling module 115 where at least a portion of the functions of scaling module 115 are performed separately on device 105-a or server 210, and/or at least a portion of the functions of scaling module 115 are performed concurrently on device 105-a and server 210.

In some configurations, the application 215 may capture one or more images via camera 120. In one embodiment, upon capturing the image, the application 215 may transmit the captured image to the server 210. In some cases, the scaling module 115 may obtain the image and may generate a scaled 3D model of the user. In one example, the scaling module 115 may transmit scaling information and/or information based on the scaled 3D model of the user to the device 105-a. In some configurations, the application 215 may obtain the scaling information and/or information based on the scaled 3D model of the object and may output a 2D image based on the scaled 3D model of the object to be displayed via the display 125.

Figure 3:
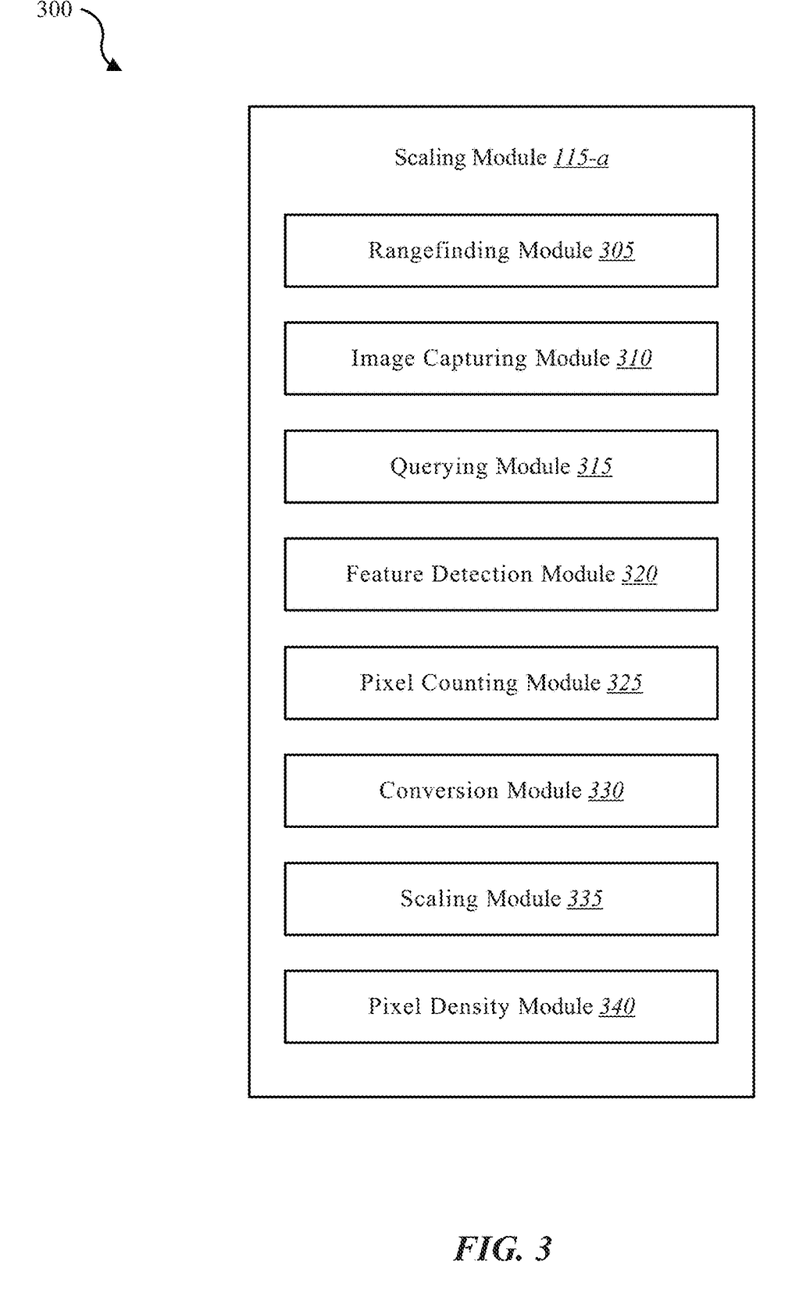
FIG. 3 is a block diagram illustrating one example of a scaling module.

FIG. 3 is a block diagram illustrating one example of a scaling module 115-a. The scaling module 115-a may be one example of the scaling module 115 illustrated in FIG. 1 or 2. The scaling module 115-a may include a range finding module 305, an image capturing module 310, a querying module 315, a feature detection module 320, a pixel counting module 325, a conversion module 330, a scaling module 335, and a pixel density module 340.

In one embodiment, rangefinder module 305 may measure a distance of an object from the mobile device. For example, rangefinder module 305 may employ optical, electroacoustic, and/or electronic means to measure a distance to an object. In some embodiments, rangefinder module 305 may include a coincidence range finder. Rangefinder module 305 may produce two or more images of an object (e.g., using mirrors and/or prisms). The rangefinder module 305 may sight the object through a viewfinder and adjust a mechanism to bring the two or more images into alignment. The rangefinder module 305 may scale the amount of adjustment to the mechanism to determine the distance to the object. In some cases, rangefinder module 305 may use coincidence and/or stereoscopic rangefinder methods. Thus, rangefinder module 305 may use a pair of eyepieces through which a single image of an object may be seen. A pattern of lines may appear to float in a space in the view of the eyepieces. A control mechanism may be adjusted until the pattern appears to be at the same distance as the object, which in turn adjusts a value on a scale. The rangefinder module 305 may read the distance to the object by reading a value on the scale that results from adjusting the control mechanism. In some cases, rangefinder module 305 may employ a laser rangefinder. A laser rangefinder may use an invisible, eye-safe Class 1 Laser beam which bounces off an object. The rangefinder module 305 may use a high-speed digital clock to measure the time it takes for the laser beam to reach the target object and return to the camera. Based on the measured time, the rangefinder module 305 may use digital electronics to calculate the distance to the target object. In some cases, the rangefinder module 305 may employ a light emitting diode (LED) rangefinder that operates in the same manner as a laser rangefinder. In some embodiments, rangefinder module 305 may employ ultrasound to measure the distance to an object similar to the way the laser rangefinder measures a laser. Thus, instead of measuring the time it takes for a laser to bounce off an object, rangefinder module 305 may emit a high-frequency sound wave towards the target object and measure the time it takes for the high-frequency sound wave to bounce off the object and return to the camera.

In one embodiment, image capturing module 310 may capture an image of the object. In some cases, image capturing module 310 may capture one or more images of the object upon determining the distance to the object via the rangefinder module 305. Upon determining the distance to the object via the rangefinder module 305, querying module 315 may query a database of pixel densities (e.g., database 110) for an image pixel density at the measured distance of the object from the mobile device. The database may contain a predetermined number of image pixel densities for a given number of distances. For example, for a camera of a given megapixel count (e.g., 1.2 MP), the pixel density of a captured image at 12 inches depth from the camera may measure to be 100 pixels per inch, at 24 inches from the camera the pixel density of the captured image may be 50 pixels per inch, and so forth.

In some embodiments, feature detection module 320 may detect a feature of the object from the captured image of the object. In some cases, detecting a feature of the object may include detecting a pupil of a user. Pixel counting module 325 may count a number of pixels associated with the detected feature of the object. Conversion module 330 may determine a distance associated with the detected feature of the object based on the number of pixels associated with the detected feature of the object. For example, the conversion module 330 may determine the distance by determining a value of a quotient resulting from dividing the number of pixels associated with the detected feature of the object by the queried pixel density at the measured distance of the object.

Determining a distance associated with the detected feature may include determining a pupil distance of the user. Thus, pixel counting module 325 may determine that the number of pixels associated with the distance between the user's pupils is 275 pixels. Querying module 315 may query a database to determine that the image pixel density at the determined distance of the user from the camera to be 100 pixels per inch. Accordingly, conversion module 330 may divide the number of pixels, 275 pixels, by the pixel density, 100 pixels per inch, to determine that there are 2.75 inches, or about 70 mm, between the user's pupils. Accordingly, scaling module 335 may scale a depiction of the object based on the determined distance associated with the detected feature of the object. For example, scaling module 335 may scale a three-dimensional model of a user based on the determined distance associated with the detected feature of the user (e.g., pupil distance). In some cases, scaling module 335 may scale a two-dimensional image of an object (e.g., a user).

In one embodiment, pixel density module 340 may determine a sensor pixel density of a camera sensor. For example, pixel density module 340 may determine the pixel density of a particular sensor is 1.2 MP. Pixel density module 340 may determine a pixel density of an image captured by the camera of the mobile device for a predetermined distance from the mobile device. In some embodiments, the pixel density module 340 may determine the pixel density of an image based at least on the sensor pixel density of the sensor and/or the sensor size. The scaling module 115-a may store the determined pixel density for each predetermined distance from the mobile device in a database (e.g., database 110).

Figure 4:
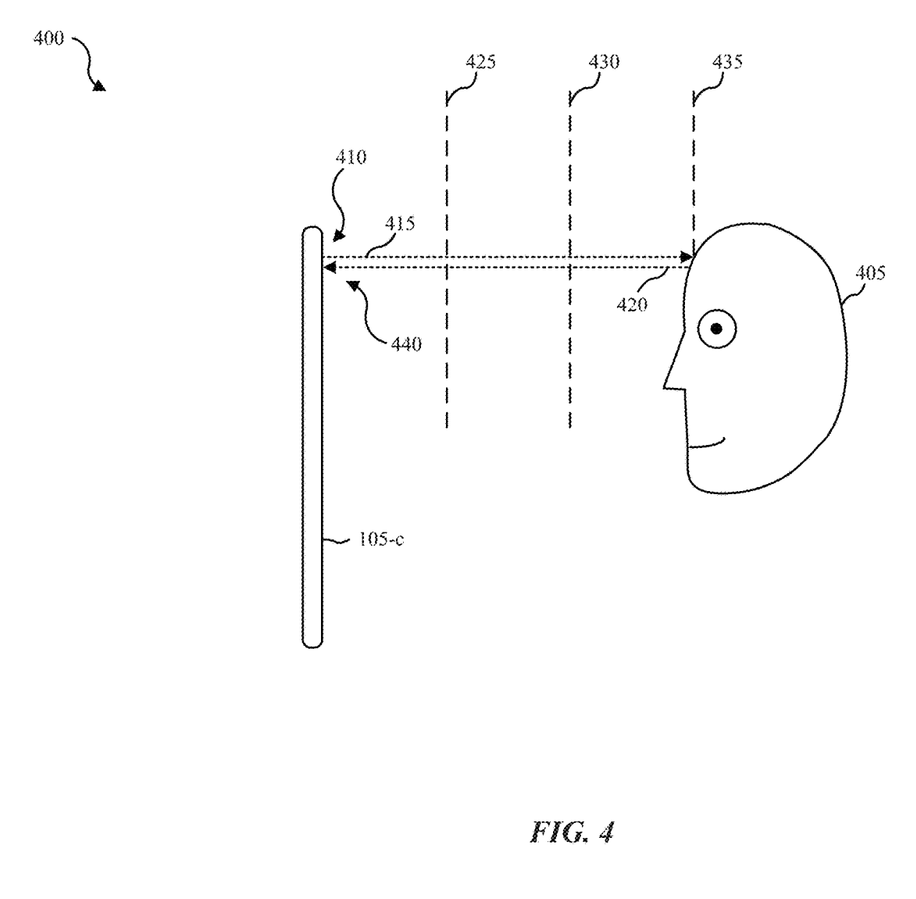
FIG. 4 is a diagram illustrating one example of a user capturing an image for use in the systems and methods described herein.

FIG. 4 is a diagram 400 illustrating an example of a device 105-b for capturing an image of an object. The depicted device 105-b may be one example of the devices 105 illustrated in FIGS. 1 and/or 2. As depicted, the device 105-b may include a camera 120-a, a rangefinder 440, and a display 125-a. The camera 120-a and display 125-a may be examples of the respective camera 120 and display 125 illustrated in FIGS. 1 and/or 2.

As depicted, device 105-b may capture an image of a user 405. At the time the image is captured (e.g., just before the image is captured, while the image is being captured, just after the image is captured, etc.), a rangefinder 440 may determine a distance between the camera 120-a and the user 405. As described above, pixel density data 135 may include information and data regarding a pixel density per unit length from the camera. For example, pixel density data 135 may include data regarding the pixel density of an image at a first distance 425, the pixel density of an image at a second distance 430, and/or the pixel density of an image at a third distance 435. For instance, it may be determined that an image of an object at the first distance 425 would have 100 pixels per inch, that an image of an object at the second distance 430 would have 50 pixels per inch, and an image of an object at the third distance 435 would have 25 pixels per inch, and so forth.

As depicted, the rangefinder 440 may emit a signal 415 towards the user 405. The emitted signal may bounce off the user 405 and a reflected signal 420 may return to the rangefinder 440. The scaling module 115 in conjunction with the rangefinder 440 may determine from the reflected signal 420 (e.g., time between emission of the emitted signal 415 and receipt of the reflected signal 420) that the user 405 is situated at a distance from the camera equivalent to the third distance 435. Accordingly, scaling module 115 may use information associated with the distance 435 between the camera 120-a and the user 405 to determine a size of a feature of the user (e.g., distance between the pupils, etc.). Scaling module 115 may use this determined size information to scale a model of the user in relation to one or more other objects.

Figure 5:
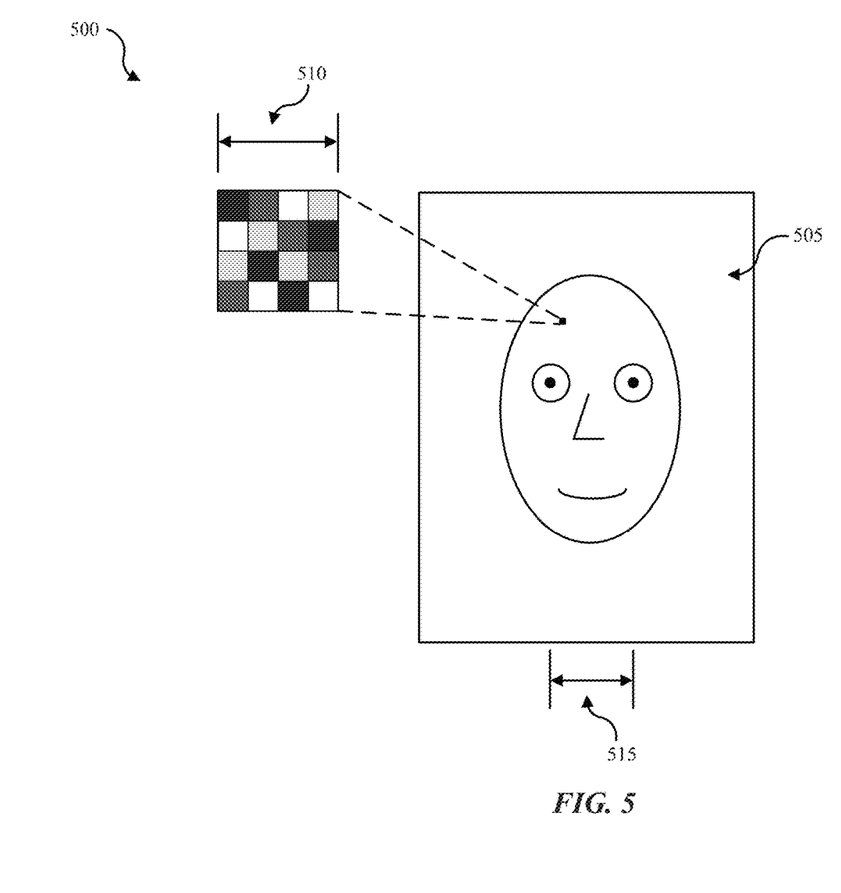
FIG. 5 is a diagram illustrating an example arrangement of a captured image of a user for use in the systems and methods described herein.

FIG. 5 is a diagram illustrating an example arrangement 500 of a captured image of a user 505 for use in the systems and methods described herein. The arrangement 500 depicts a front view of an image of a user 505. In one embodiment, the image of the user 505 may represent a resultant image of user 405 captured by camera 120-a in relation to the arrangement of FIG. 4. In some embodiments, scaling module 115 may determine the pixel density (e.g., pixels per inch, pixels per millimeter, etc.) associated with a detected feature of an object, where the pixel density is determined in relation to a determined distance of the object from the camera when the image was captured. In some cases, scaling module 115 may determine that distance 510 represents the numbers of pixels per millimeter. For example, as depicted, scaling module 115 may determine there are four pixels per millimeter in relation to a determined distance between the camera and a detectable feature of the user. Thus, a distance 515 between two points on the image of the user (e.g., pupil distance) may be determined based on the determined pixel density of the image 505 at the determined distance between the user and the camera. For example, scaling module 115 may determine that there are 280 pixels between the two points that make up the distance 515. Knowing the distance between the user and the camera (e.g., distance 435 of FIG. 4), scaling module 115 may determine that there are 4 pixels per mm in image 505 at that determined distance between the user and the camera. Accordingly, scaling module 115 may determine the quotient that results by dividing the number of pixels between distance 515 (e.g., 280 pixels) by the determined pixel density (e.g., 4 pixels per mm) to determine that the distance 515 is equivalent to a value around 70 mm. Based on this determined distance, scaling module 115 may scale a model of the user, as described above.

Figure 6:
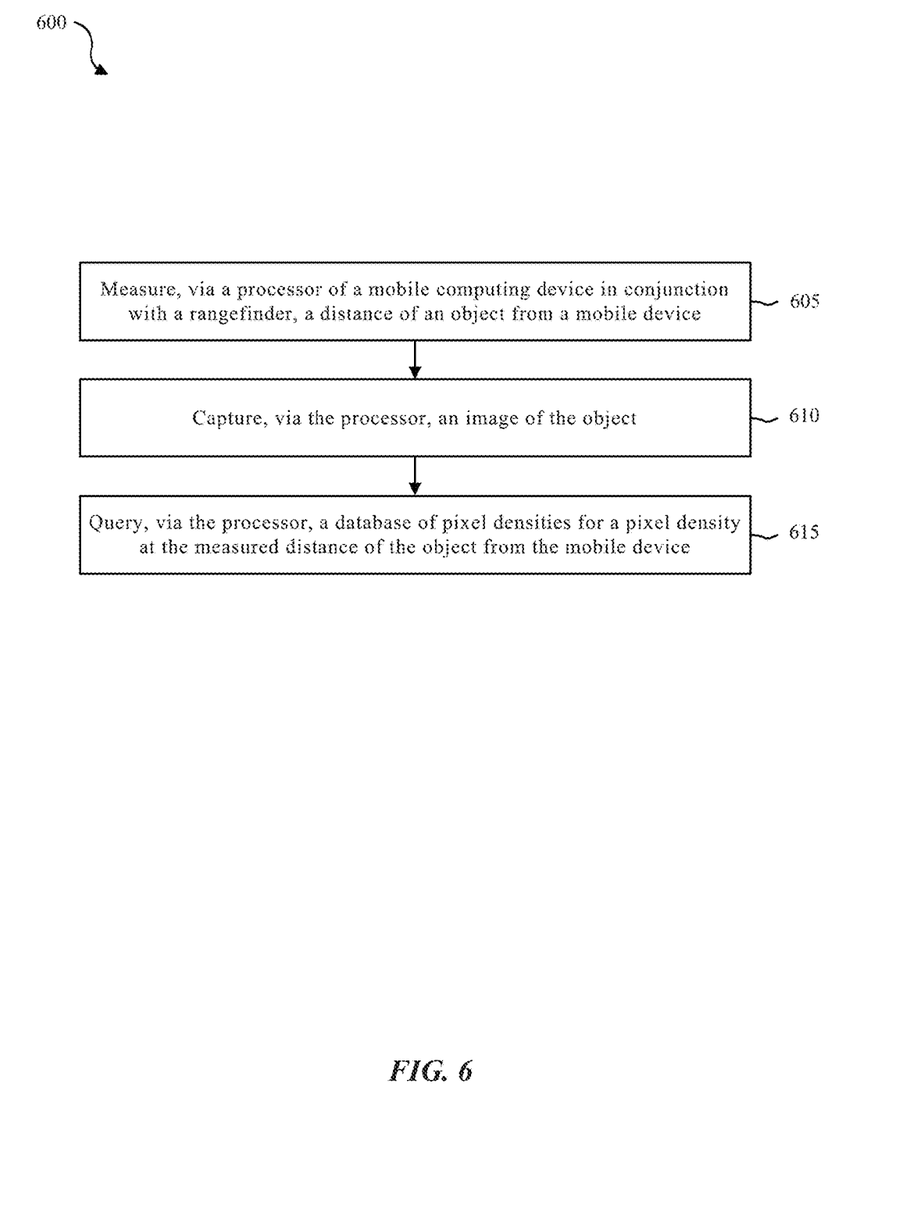
FIG. 6 is a flow diagram illustrating one example of a method for scaling a model of an object based on a determined distance of the object from a camera when an image of the object is captured.

FIG. 6 is a flow diagram illustrating one example of a method 600 for determining a distance between a camera and an object whose image is being captured by a camera. In some configurations, the method 600 may be implemented by the scaling module 115 illustrated in FIG. 1, 2, or 3.

At block 605, a distance of an object from a mobile computing device may be measured via a processor of the mobile computing device in conjunction with a rangefinder. At block 610, an image of the object may be captured via the processor. At block 615, a database of pixel densities for a pixel density at the measured distance of the object from the mobile device may be queried via the processor.

Figure 7:
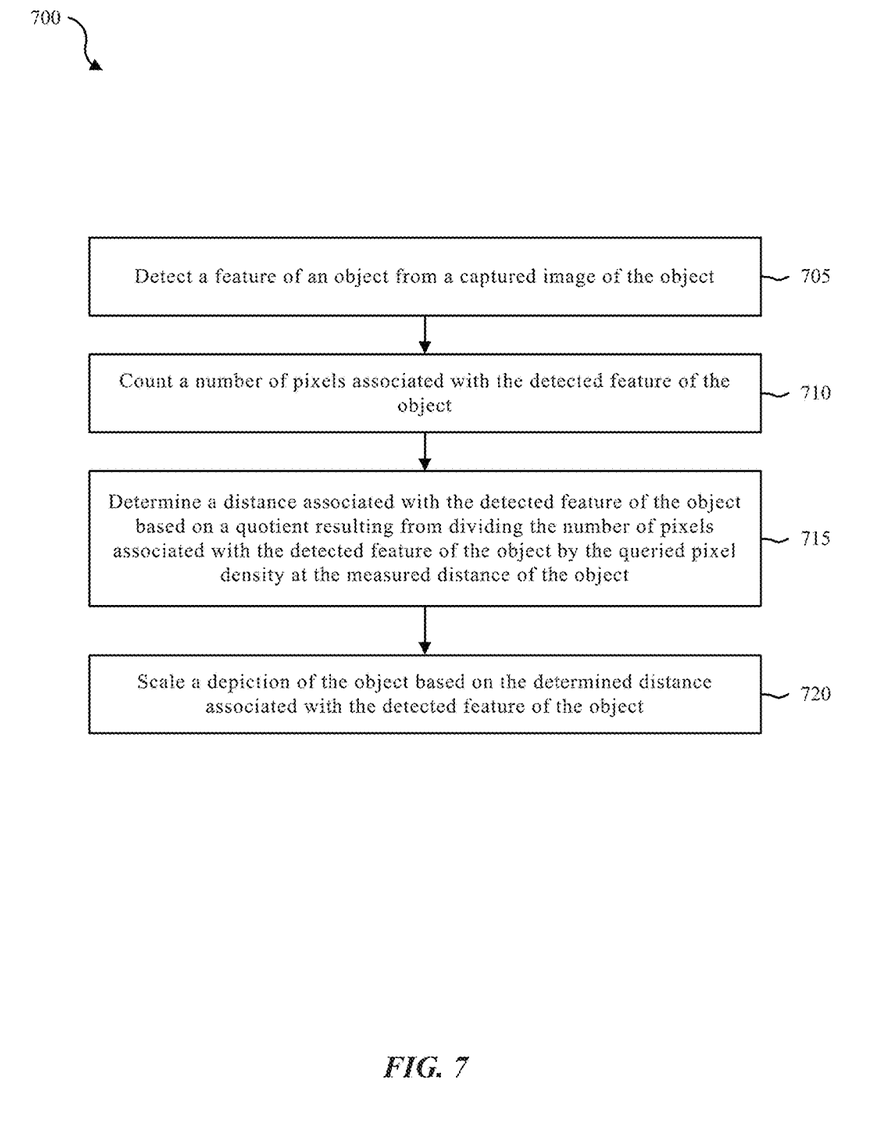
FIG. 7 is a flow diagram illustrating one example of a method for calibrating a mobile device to determine a unit of length in relation to an image of an object based on a determined distance of the object from the camera.

FIG. 7 is a flow diagram illustrating one example of a method 700 for scaling a model of an object based on a determined distance of the object from a camera when an image of the object is captured. In some configurations, the method 700 may be implemented by the scaling module 115 illustrated in FIG. 1, 2, or 3.

At block 705, a feature of an object may be detected from an image of the object. In some cases, detecting a feature of the object may include detecting a pupil of a user. At block 710, a number of pixels associated with the detected feature of the object may be counted. At block 715, a distance associated with the detected feature of the object may be determined based on a quotient resulting from dividing the number of pixels associated with the detected feature of the object by the queried pixel density at the measured distance of the object. In some cases, determining a distance associated with the detected feature may include determining a pupil distance of the user. At block 720, a depiction of the object may be scaled based on the determined distance associated with the detected feature of the object.

Figure 8:
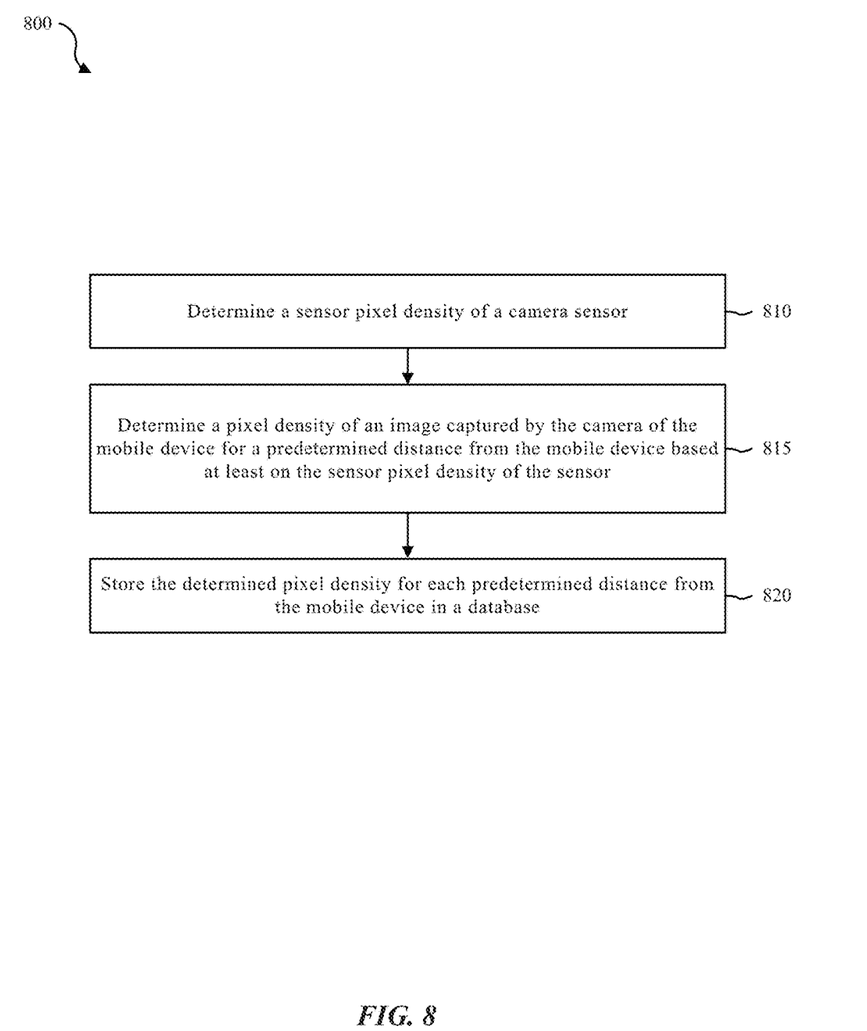
FIG. 8 is a flow diagram illustrating another example of a method to scale a 3D model.

FIG. 8 is a flow diagram illustrating another example of a method 800 for calibrating a mobile device to determine a unit of length in relation to an image of an object based on a determined distance of the object from the camera. In some configurations, the method 800 may be implemented by the scaling module 115 illustrated in FIG. 1, 2, or 3.

At block 805, a sensor pixel density of a camera sensor may be determined. At block 810, a pixel density of an image captured by the camera of the mobile device may be determined for a predetermined distance from the mobile device based at least on the sensor pixel density of the sensor. At block 815, the determined pixel density may be stored for each predetermined distance from the mobile device in a database.

Figure 9:
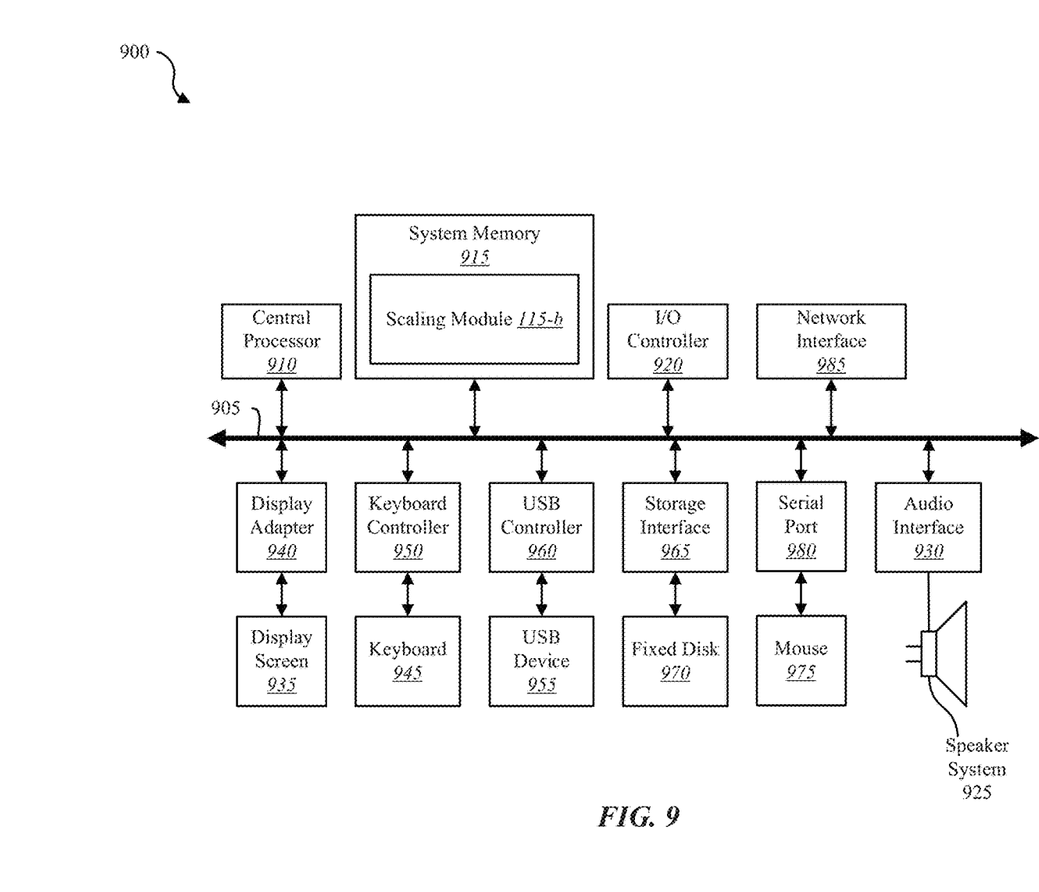
FIG. 9 depicts a block diagram of a computer system suitable for implementing the present systems and methods.

FIG. 9 depicts a block diagram of a computer system 900 suitable for implementing the present systems and methods. For example, the computer system 900 may be suitable for implementing the device 105 illustrated in FIG. 1, 2, or 6 and/or the server 210 illustrated in FIG. 2. Computer system 900 includes a bus 905 which interconnects major subsystems of computer system 900, such as a central processor 910, a system memory 915 (typically RAM, but which may also include ROM, flash RAM, or the like), an input/output controller 920, an external audio device, such as a speaker system 925 via an audio output interface 930, an external device, such as a display screen 935 via display adapter 940, a keyboard 945 (interfaced with a keyboard controller 950) (or other input device), multiple universal serial bus (USB) devices 955 (interfaced with a USB controller 960), and a storage interface 965. Also included are a mouse 975 (or other point-and-click device) interfaced through a serial port 980 and a network interface 985 (coupled directly to bus 905).

Bus 905 allows data communication between central processor 910 and system memory 915, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. For example, the scaling module 115-b to implement the present systems and methods may be stored within the system memory 915. Applications (e.g., application 215) resident with computer system 900 are generally stored on and accessed via a non-transitory computer readable medium, such as a hard disk drive (e.g., fixed disk 970) or other storage medium. Additionally, applications can be in the form of electronic signals modulated in accordance with the application and data communication technology when accessed via interface 985.

Storage interface 965, as with the other storage interfaces of computer system 900, can connect to a standard computer readable medium for storage and/or retrieval of information, such as a fixed disk drive 944. Fixed disk drive 944 may be a part of computer system 900 or may be separate and accessed through other interface systems. Network interface 985 may provide a direct connection to a remote server via a direct network link to the Internet via a POP (point of presence). Network interface 985 may provide such connection using wireless techniques, including digital cellular telephone connection, Cellular Digital Packet Data (CDPD) connection, digital satellite data connection, or the like.

Many other devices or subsystems (not shown) may be connected in a similar manner (e.g., document scanners, digital cameras, and so on). Conversely, all of the devices shown in FIG. 9 need not be present to practice the present systems and methods. The devices and subsystems can be interconnected in different ways from that shown in FIG. 9. The operation of a computer system such as that shown in FIG. 9 is readily known in the art and is not discussed in detail in this application. Code to implement the present disclosure can be stored in a non-transitory computer-readable medium such as one or more of system memory 915 or fixed disk 970. The operating system provided on computer system 900 may be iOS®, MS-DOS®, MS-WINDOWS®, OS/2®, UNIX®, Linux®, or another known operating system.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon."

What is claimed is:

1. A computer-implemented method for scaling an object, the method comprising:
    measuring, via a processor of a computing device in conjunction with a rangefinder, a distance of the object from the computing device;
    capturing, via the processor, an image of the object;
    querying, via the processor, a database of pixel densities for a pixel density at the measured distance of the object from the computing device;
    detecting, via the processor, a first feature of the object;
    determining, via the processor, a number of pixels associated with the detected first feature of the object; and
    determining, via the processor, a size associated with the detected first feature of the object based on the number of pixels associated with the detected first feature of the object, wherein determining the size comprises determining a quotient resulting from dividing the number of pixels associated with the detected first feature of the object by the queried pixel density at the measured distance of the object.

2. The method of claim 1, further comprising:
    determining the size by calculating a distance associated with the detected first feature of the object based on a quotient resulting from dividing the number of pixels associated with the detected first feature of the object by the queried pixel density at the measured distance of the object.

3. The method of claim 1, further comprising:
    scaling a depiction of the object based on the determined size associated with the detected first feature of the object.

4. The method of claim 1, further comprising:
    determining a sensor pixel density of a sensor.

5. The method of claim 4, further comprising:
    determining a pixel density of an image captured by a camera of the computing device for a predetermined distance from the computing device based at least on the sensor pixel density of the sensor.

6. The method of claim 5, further comprising:
    storing the determined pixel density for each predetermined distance from the computing device in the database.

7. The method of claim 1, wherein the detecting the first feature of the object comprises detecting a pupil of a user.

8. A computing device configured to scale an object, comprising:
    a processor;
    memory in electronic communication with the processor;
    instructions stored in the memory, the instructions being executable by the processor to:
        measure, in conjunction with a rangefinder of the computing device, a distance of the object from the computing device;
        capture an image of the object;

query a database of pixel densities for a pixel density at the measured distance of the object from the computing device;
detect a first feature of the object;
determine a number of pixels associated with the detected first feature of the object; and
determine a size associated with the detected first feature of the object based on the number of pixels associated with the detected first feature of the object, based on a quotient resulting from dividing the number of pixels associated with the detected first feature of the object by the queried pixel density at the measured distance of the object.

9. The computing device of claim 8, wherein the instructions are further executable by the processor to:
determine the size by calculating a distance associated with the detected first feature of the object based on a quotient resulting from dividing the number of pixels associated with the detected first feature of the object by the queried pixel density at the measured distance of the object.

10. The computing device of claim 8, wherein the instructions are further executable by the processor to:
scale a depiction of the object based on the determined size associated with the detected first feature of the object.

11. The computing device of claim 8, wherein the instructions are further executable by the processor to:
determine a sensor pixel density of a sensor.

12. The computing device of claim 11, wherein the instructions are further executable by the processor to:
determine a pixel density of an image captured by a camera of the computing device for a predetermined distance from the computing device based at least on the sensor pixel density of the sensor; and
store the determined pixel density for each predetermined distance from the computing device in the database.

13. The computing device of claim 8, wherein the instructions executable by the processor to detect the first feature of the object comprise instructions executable by the processor to detect a pupil of a user.

14. The computing device of claim 13, wherein the instructions executable by the processor to determine the size associated with the detected first feature comprise instructions executable by the processor to determine a distance between pupils of the user.

15. A computer-program product for scaling, via a processor, an object, the computer-program product comprising a non-transitory computer-readable medium storing instructions thereon, the instructions being executable by the processor to:
measure, in conjunction with a rangefinder, a distance of an object from a computing device;
capture an image of the object;
query a database of pixel densities for a pixel density at the measured distance of the object from the computing device;
detect a feature of the object;
determine a number of pixels associated with the detected feature of the object; and
determine a distance associated with the detected feature of the object, wherein the distance associated with the detected feature of the object is determined based on a quotient resulting from dividing the number of pixels associated with the detected feature of the object by the queried pixel density at the measured distance of the object.

16. The method of claim 1, further comprising:
detecting a second feature of the object; and
determining a distance between the detected first feature of the object and the detected second feature of the object based on a quotient resulting from dividing the number of pixels between the detected first feature of the object and the detected second feature of the object by the queried pixel density at the measured distance of the object.

17. The method of claim 16, wherein:
the detecting the first feature of the object comprises detecting a first pupil of a user;
the detecting the second feature of the object comprises detecting a second pupil of the user; and
the determining the distance between the detected first feature of the object and the detected second feature of the object comprises determining a distance between the first and second pupils of the user.

18. The computing device of claim 8, wherein the instructions are further executable by the processor to:
detect a second feature of the object; and
determine a distance between the detected first feature of the object and the detected second feature of the object based on a quotient resulting from dividing the number of pixels between the detected first feature of the object and the detected second feature of the object by the queried pixel density at the measured distance of the object.

* * * * *